(12) United States Patent
Docquier

(10) Patent No.: US 8,220,291 B2
(45) Date of Patent: Jul. 17, 2012

(54) METHOD FOR MONITORING BY ABSORPTION SPECTROSCOPY DURING THE FORMING OF FLAT GLASS AND MONITORING DEVICE

(75) Inventor: Nicolas Docquier, Philadelphia, PA (US)

(73) Assignee: L'Air Liquide Societe Anonyme pour l'Etude et l'Exploitation des Procedes Georges Claude, Paris (FR)

(*) Notice: Subject to any disclaimer, the term of this patent is extended or adjusted under 35 U.S.C. 154(b) by 918 days.

(21) Appl. No.: 12/063,311

(22) PCT Filed: Aug. 9, 2006

(86) PCT No.: PCT/FR2006/050794
§ 371 (c)(1),
(2), (4) Date: Feb. 8, 2008

(87) PCT Pub. No.: WO2007/017616
PCT Pub. Date: Feb. 15, 2007

(65) Prior Publication Data
US 2010/0162766 A1 Jul. 1, 2010

(30) Foreign Application Priority Data
Aug. 11, 2005 (FR) .................. 05 52490

(51) Int. Cl.
*C03B 9/41* (2006.01)
*G01B 21/00* (2006.01)
*G01K 11/00* (2006.01)

(52) U.S. Cl. .................. 65/158; 356/437; 374/161
(58) Field of Classification Search .......... 65/158; 356/437; 374/161
See application file for complete search history.

(56) References Cited

U.S. PATENT DOCUMENTS

| 5,880,850 | A | * | 3/1999 | McAndrew et al. | 356/437 |
| 6,154,284 | A | * | 11/2000 | McAndrew et al. | 356/437 |
| 6,493,086 | B1 | * | 12/2002 | McAndrew et al. | 356/437 |
| 2002/0031737 | A1 | * | 3/2002 | Von Drasek et al. | 431/79 |
| 2003/0218752 | A1 | * | 11/2003 | Drasek et al. | 356/439 |
| 2007/0062218 | A1 | * | 3/2007 | Champinot et al. | 65/29.12 |

FOREIGN PATENT DOCUMENTS

| WO | WO 01/33200 | 5/2001 |
| WO | WO 2005/023720 | 3/2005 |

* cited by examiner

*Primary Examiner* — Matthew Daniels
*Assistant Examiner* — Russell Kemmerle, III
(74) *Attorney, Agent, or Firm* — Christopher J. Cronin

(57) ABSTRACT

The invention relates to a method for controlling flat glass forming by flowing a molten glass over a liquid tin layer contained in a forming vat wherein a forming characteristic quantity is measured above the glass surface during forming by means of beams generated by at least one absorption spectroscopy-based analyser, wherein the light beams generated by said analyser form a net above the glass surface. A device for carrying out the inventive method comprising an arm for supporting a vessel which comprises a retroreflecting means for receiving a light beam and transmitting it in an opposite direction parallel to an incident optical path is also disclosed.

5 Claims, 2 Drawing Sheets

Figure 1:
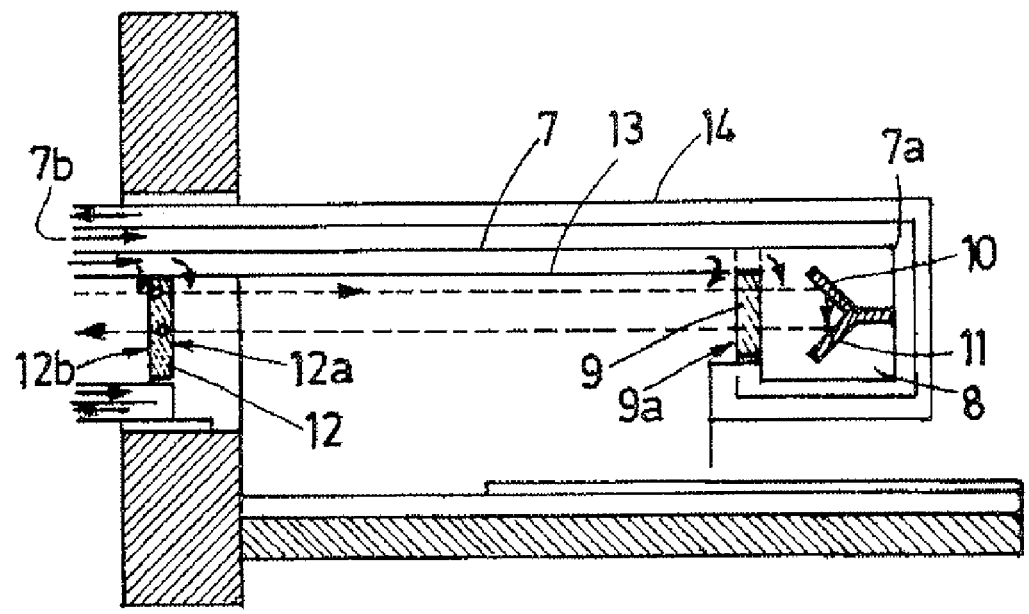

METHOD FOR MONITORING BY ABSORPTION SPECTROSCOPY DURING THE FORMING OF FLAT GLASS AND MONITORING DEVICE

This application is a 371 of International PCT Application PCT/FR2006/050794, filed Aug. 9, 2006.

BACKGROUND

The present invention relates to a method for monitoring the forming of flat glass by flow of molten glass over a sheet of liquid tin.

The method for forming flat float glass consists in introducing the hot glass exiting from a melting furnace over a sheet of liquid tin held in a tank. The tank is composed of a metal chamber, the walls of which are lined with a refractory material. The glass spreads over the denser tin up to a thickness of approximately 6 mm conditioned by the combined effect of gravitational force, surface tension force and tensile force. The latter force is exerted by the support rolls of the solidified glass ribbon in the annealing lehr situated downstream of the tin tank.

The forming of flat glass is carried out under an atmosphere comprising nitrogen and hydrogen (3 to 10% by volume of the atmosphere) in order to limit the oxidation of the tin under the effect of air entering in small amounts, from the degassing of the glass, and of residual entities in the nitrogen and hydrogen introduced, such as water. This atmosphere is maintained at a slightly positive pressure and is replaced continuously in order to prevent the accumulation of impurities which can cause defects in the glass.

The presence of water and oxygen contaminates the tin and results in the emission of stannous oxide (SnO) into the atmosphere. This stannous oxide can condense on the refractory walls in the downstream part of the tank and, by chemical reduction, can fall as metal drops onto the glass ribbon. In addition, the increase in the content of dissolved oxygen in the tin bath results in the absorption of increasing amounts of stannous oxide on the lower face of the glass ribbon. If these amounts are too high, this stannous oxide can be converted to stannic oxide during the subsequent heat treatments of the glass ribbon and can form a bluish bloom on the glass. Finally, as the solubility of oxygen is strongly correlated with the temperature (from 630 to 5 ppm when the tin changes from 1000 to 600° C.) and as the forward progression of the glass results in the rapid movement of the tin from the hot upstream region (1000° C.) to the cold downstream region of the tank (600° C.), the oxygen dissolved in the hot region can precipitate as stannic oxide in the cold part of the tank and cause gradual fouling of the tin bath.

In order to avoid these problems, it is known to adjust the heating profile in the tank roof and the distribution of the nitrogen and hydrogen streams (in the form of a stream of nitrogen/hydrogen mixture and optionally of pure nitrogen) as a function of the operating conditions: pull of glass product, taking the temperature at localized points in the chamber, measurement of the thickness of the glass and monitoring of the change over time in the level of original defects due to the tin. It is also essential to measure the concentration of water vapor in the atmosphere (or dew point) above the bath as there exists a direct correlation between the quality of the glass and the dew point level above the glass sheet in the forming region. This dew point must be maintained at the lowest level in order to prevent contamination of the glass sheet by the tin or its oxides. The increase in the dew point can result from a lack of leaktightness, from escape of water on one of the elements inserted inside the chamber (for example, a cooler) or from a failing in inerting the chamber (excessively low pressure, excessively high level of impurity or poor adjustment of the $N_2/H_2$ ratio).

In all cases, the operators have to act very rapidly in order to prevent an absolute loss in production. In point of fact, the speed of reaction depends on the accuracy of the diagnosis. It is therefore important to be able to locate with the greatest possible accuracy the point in the tank where a problem is rife.

Application WO 2005/023720 describes a method for monitoring the forming of flat glass by flow of molten glass over a sheet of liquid tin, in which the concentration of $H_2O$ above the surface of the glass during forming is measured using at least one laser diode. In point of fact, the measurement obtained by the laser diode is averaged along the optical path traveled by the beam inside the tin tank. It is difficult to specify at what point on this path the concentration of water vapor is highest. Moreover, as the diodes are oriented perpendicularly to the direction of forward progression of the glass sheet, it is not possible to indicate on what side of the tank it is necessary to intervene.

The objective of the present invention is to provide an improvement to the method for monitoring the forming of flat glass by measuring a quantity characteristic of the forming, such as $H_2O$ concentration, said improvement making it possible to more accurately locate the point where the characteristic quantity is changing and thus to reduce the time for the operators to intervene.

With this objective, the invention relates to a method for controlling the forming of flat glass by flow of molten glass over a sheet of liquid tin present in a forming tank, in which a characteristic forming quantity, such as $H_2O$ concentration, is measured above the surface of the glass during forming using light beams generated by at least one analyzer based on absorption spectroscopy and in which at least two beams generated by the analyzer intersect above the surface of the glass.

The invention applies to any method which employs monitoring of the forming process using an analyzer operating by emission of a mono- or polychromatic light wave through the atmosphere of the tank to be analyzed and then reception of this wave and comparison with the emitted wave, said comparison making it possible to deduce the presence of compounds in the atmosphere through which the wave has passed. Use is advantageously made of an analyzer which makes it possible to measure the concentration of gas exhibiting a temperature of greater than 300° C. It is also preferable to use analyzers capable of giving reliable measurements in a medium exhibiting a temperature gradient which may be high and rise up to 500° C. The main invention applies particularly to an analyzer which is a laser diode. In the context of the present invention, the term "laser diode" is understood to mean an analyzer which is composed:
- of a source comprising a generator of the laser beam having a wavelength which can vary within a range of wavelengths $\Delta\lambda$ which encompasses at least one absorption line characteristic of the entity whose presence it is desired to detect, and
- of an emitter which directs the beam into the medium to be analyzed,
- of the receiver of this beam after it has passed through the medium to be analyzed, and
- of means of comparison, for example, of the amplitude of the laser beam received (intensity of the beam) and of the amplitude of the laser beam emitted throughout the range of wavelengths under consideration. In the description which follows, the definitions of generator, emitter and receiver above are generalized to any type of analyzer by absorption spectroscopy.

The characteristic quantity of the process can be the concentration of water, of oxygen or of SnO. Preferably, it is the concentration of water and the analyzer is a laser diode.

By implementation of the invention, the measurement is carried out using at least one analyzer generating light beams which intersect above the surface of the glass. By virtue of the intersections of the beams, it is possible to rapidly locate the place where, for example, the concentration of $H_2O$ increases. This is because the operator deduces from the analyzers of the beams indicating a rise in concentration of $H_2O$ that the scene of this rise is at the intersection of the beams of these analyzers. This deduction can be made using a monitoring logical operator or an automatic operator for helping with the decision. According to the invention, the plane formed by the beams is parallel to the plane of flow of the flat glass. The surface of the glass can thus be marked out in squares; however, the invention is not targeted at obtaining a detailed description in the atmosphere in a given plane but at guaranteeing that, at the key points in the forming tank, the information necessary and sufficient for understanding and optimizing the operation of the process is obtained.

According to the preferred implementation of the invention, at least one beam is directed perpendicularly to the direction of flow of the molten glass and at least one beam is directed parallel to the direction of flow of the molten glass. This implementation makes it possible to mesh a point of the surface of the glass; it is thus possible to monitor the concentration of a contaminating entity at this precise point and to deduce increases in concentration in regions between these points. This is because, if two beams which intersect detect an increase in concentration, then this increase is situated at their intersection. If a single beam detects an increase in concentration, then the increase in temperature is situated at a point situated on its optical path and placed outside its intersections with the other beams. According to the invention, the terms "perpendicular beams" and "parallel beams" are understood to mean beams, the directions of which are overall parallel or perpendicular to the direction of flow of the molten glass.

Preferably, use is made of at least one of the three following beams perpendicular to the direction of flow of the molten glass:
- one of the beams directed perpendicularly to the direction of flow of the molten glass is placed in the hot and upstream region of the tank,
- one of the beams directed perpendicularly to the direction of flow of the molten glass is placed in the cold and downstream region of the tank,
- one of the beams directed perpendicularly to the direction of flow of the molten glass is placed in the middle of the tank. The latter beam directed perpendicularly to the direction of flow of the molten glass and placed in the middle of the tank is preferably situated at the point in the tank where the region of the gases captured towards the upstream of the tank and the region of the gases captured towards the downstream of the tank divide. The beams placed in the upstream and downstream regions are close to the conditioning zone and annealing lehr; hence the leaktightness may not be complete and is compensated for only by a slight excess pressure in the tank. The beams placed upstream also make it possible to take into account the variations in atmosphere close to the machines which are present there, such as carbon barriers, top rollers and coolers. The beams placed downstream finally also make it possible to take into account the variations in atmosphere close to the many coolers intended to produce the coldest possible temperatures and which can result in the condensation of tin oxides responsible for damage to the quality of the glass.

As regards the beam directed parallel to the direction of flow of the molten glass, it is preferably placed close to one of the walls of the tank. According to a preferred form, two beams of this type are placed on each side of the tank. This type of beam is generally placed at 10 to 200 cm from the edge of the tank. This is because it is close to the boundaries of the chamber that air can seep through: in particular, close to the region of the side sealing composed on both sides of the tank (left and right sides) of sealing boxes making it possible either to fill in the empty spaces or to arrange a peephole or to position the machines necessary for the forming of the glass sheet (coolers, top rollers, carbon barriers, and the like).

Preferably, at least two beams generated by the analyzer intersect above the surface of the glass close to the interfaces between the sealing boxes and the machines necessary for the forming of the glass sheet. This is because air and water present in the cooling systems of said forming machines can seep into the tank at this point.

In practice, it is possible to use a single beam generator to generate all the beams of the network, for example by splitting up the beam of the only generator or by rapidly switching the beam of the generator over several measurement points (it is sufficient for the speed of switching to be high with respect to the time scales characteristic of the process for forming the glass, that is to say a few seconds at most). It is also possible to use several generators each generating a beam.

For a beam directed perpendicularly to the direction of flow of the molten glass, the emitter and the receiver of the analyzers are generally placed outside the tank and on each side of the latter. The beam penetrates and exits from the tank via sighting windows made in the wall of the tank at a height such that the beam passes at a short distance above the surface of the glass in the course of forming. The emitter and the receiver are positioned behind each of these sighting windows. According to an alternative form, the emitter and the receiver can be placed behind the same sighting window; an optical backreflecting device, for example a set of mirrors, is placed behind the second sighting window so as to reflect the beam emitted by the emitter towards the receiver. An inert gas, such as nitrogen, is generally used to clean the surface of the sighting windows of the emitter and of the receiver and optionally of the mirror, in order to avoid the deposition of dust, to prevent excessive heating of the emitter and of the receiver and/or to avoid any interference with ambient moisture (that is to say, outside the tank).

Depending on the nature of the tank, for a beam directed parallel to the direction of flow of the molten glass, the beam is directed by an emitter and a receiver which are placed in the downstream and central shoulders of the tank. As above, the emitter and the receiver of the analyzers are placed outside the tank upstream of the latter and in the central shoulder of the latter. However, if the tank does not exhibit a shoulder, it is possible to guide the beams directed parallel to the direction of flow of the molten glass (whether they are upstream or downstream of this shoulder) via at least one mirror. For example, the beam enters the furnace via a sighting window made in the longitudinal wall of the tank or in the roof of the tank and thus perpendicular to the direction of flow of the glass. This beam is then redirected so as to be parallel to the direction of flow of the glass by means of a mirror present in the tank and oriented at 45° to the beam striking it, so as to guide it towards the sighting window of the receiver. The mirror is placed in the tank by means of an arm, cooled beforehand, passed through the wall of the tank. The use of such an arm equipped with a mirror is particularly advantageous as it makes it possible to monitor the concentration of $H_2O$ as close as possible (at a distance of between 0.1 and 2 m from the internal wall of the tank) to the longitudinal wall of the tank, at the point where problems of leaktightness are common.

According to an alternative form, the characteristic quantity of the process measured is the temperature of the atmosphere above the surface of the glass.

The laser diode can be placed at a distance from the surface of the glass in the course of forming of between 2 and 50 cm, preferably between 5 and 20 cm.

The invention also relates to the use of the preceding method for locating a contaminated region above the tin bath.

The invention also relates to a device capable of being used for the implementation of the method described above, comprising:
- an arm, a first end of which supports a box:
  - the wall of said box placed facing the second end of the arm is transparent, and
  - within which is placed a backreflecting means capable of receiving a light beam originating from the first end of the arm and parallel to said arm and of returning it in the opposite direction parallel to the incident optical path,
- a transparent screen attached to the second end of the arm so as to face the transparent wall of the box,
- a means for introducing gas close to the surfaces of the transparent wall and of the transparent screen and optionally in the box,
- a means for cooling the arm and the box.

In the present invention, the term "transparent wall" is understood to mean a wall which is transparent at the wavelength(s) of the beam of the analyzer.

The detailed description and the operation of this device are made in connection with FIG. 1. This device is thus composed of an arm 7, that is to say of a rod, one end 7a of which carries a box 8. Preferably, the arm exhibits a length such that the transparent wall 9 of the box is situated between 0.2 and 2 m from the internal wall of the tank, preferably between 0.5 and 2 m. The box 8 is preferably leaktight to gases and filled with an inert gas. It comprises at least one transparent wall 9 and includes a backreflecting means capable of receiving a beam of incident light and of returning it along an optical path essentially parallel to the incident beam. In FIG. 1, this backreflecting means is an optical system composed of two mirrors 10 and 11. These two mirrors 10 and 11 are arranged in order to ensure that a beam (dotted line) passing through the transparent wall 9 of the box 8 falls on the surface of a mirror. Due to the arrangement of the mirrors at 90°, the first mirror 10 sends the optical beam to the second mirror 11, which returns the optical beam through the transparent wall 9 along a direction parallel to the incident beam. Any other backreflecting means can be used, such as, for example, one or more prisms. The beam passes, on the outward journey and on the return journey, through a transparent screen 12 situated on the second edge 7b of the arm. Preferably, the box and the transparent screen are attached perpendicularly to the arm. The device is equipped with a means 13 for introducing gas close to the surfaces of the transparent wall 9 and of the screen 12 and preferably at the following points:
- at the face 12a of the screen and at the face 9a of the transparent wall which face one another and which are intended to be placed in the atmosphere of the tin tank, so as to prevent the deposition of impurities on these faces,
- at the face 12b of the screen 12, so as to avoid the presence of absorbent molecules on the optical path of the beams between this face 12b and the analyzer, it being possible for said molecules to distort the measurement of the characteristic quantity of the method,
- and, finally, optionally in the box 8 if the latter is not leaktight, as is represented in FIG. 1.

The gas introduced is an inert gas, such as nitrogen, argon or helium, which cannot be oxidized within the temperature range of the forming in the tin tank or which does not react with any of the compounds present in the atmosphere above the tin bath. The device is also equipped with a means 14 for cooling the arm 7 and the box 8 in order to prevent them from being damaged during their introduction into the forming tank. This cooling means consists, for example, in circulating water in a jacket surrounding the arm and the box.

Finally, the invention relates to the use of the above device for measuring a quantity in a furnace using a light beam generated by at least one analyzer based on absorption spectroscopy, said beam being directed through the transparent screen and parallel to the arm.

The analyzer is preferably a laser diode. The quantity can be chosen from: the concentration of a chemical compound or the temperature of the atmosphere in the furnace.

This use is particularly suited to a glass melting furnace, in particular to the method for monitoring the forming of flat glass in order to probe each point of the network, and very particularly for the taking of measurements in the downstream region of the tank, which is more difficult to access by a longitudinal beam. For example, the device is then placed downstream of a shoulder of the tank. This device is introduced via an opening of a wall of the tank and the emitter and the receiver of a laser diode are placed behind the transparent screen 12 attached to the second end 7b of the arm. By means of the device, the beam performs a round trip above the surface of the glass. By virtue of the cooling means 14, the device can be installed in the high-temperature tank throughout the time of the measurements to be carried out. The means 13 for introducing gas makes it possible to circulate an inert gas in the box 8 where the backreflecting means is positioned or to create therein an excess pressure of this inert gas with respect to the pressure in the tank, close to the face 12a of the screen and of the face 9a of the transparent wall and between the screen 12 and the analyzer. This inert gas makes it possible to prevent the deposition of impurities on the transparent walls and to avoid the presence of molecules of the surrounding atmosphere which are introduced with the device during its installation in the tank. This device exhibits the advantage of being able to be easily introduced into and removed from the tank without having to restart realignment operations between the emitter and the receiver of the same analyzer. It also exhibits the advantage of giving a virtually local measurement in the vicinity of the wall of the tank.

Figure 2:
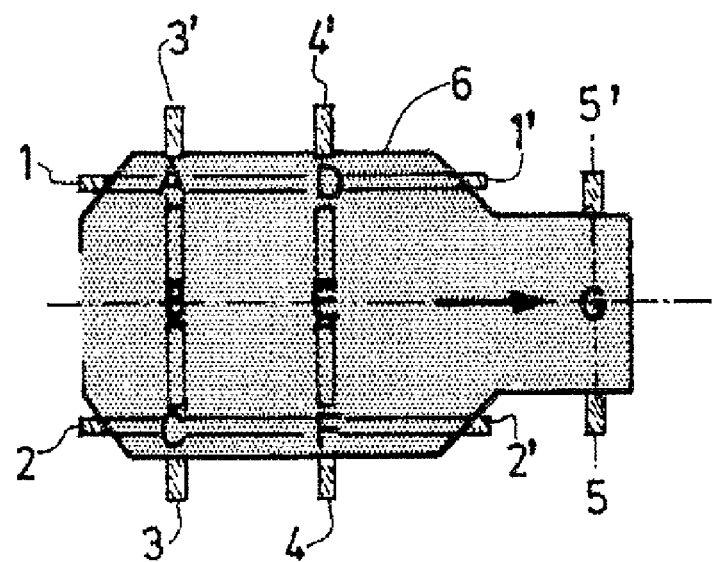

FIG. 2 illustrates the implementation of the method according to the invention. The figure is a top view of a glass forming tank 6. Three analyzer emitter/receiver pairs 3/3', 4/4', 5/5' make it possible to measure a characteristic quantity of the process above the glass surface. Their beams are directed perpendicularly to the direction of the flow of the glass in three regions: in an upstream region, in the middle and in a downstream region. Use is also made of two other emitter/receiver pairs 1/1', 2/2' placed in the central shoulder and the upstream wall of the tank; their beams are directed parallel to the direction of the flow of the glass: close to each wall of the tank 6. By virtue of the five beams, a network of six points (A to F) and of a region G of the surface of the glass is obtained. According to the signals given by each analyzer (1: abnormal measurement of the characteristic quantity, 0: normal measurement of the characteristic quantity), it is possible to rapidly determine where the problem related to the characteristic quantity is located, as is exemplified in the following table:

| Analyzer | Signals of the analyzers | | | | | | |
|---|---|---|---|---|---|---|---|
| 1/1' (left) | 1 | 0 | 0 | 1 | 0 | 0 | 0 |
| 2/2' (right) | 0 | 0 | 1 | 0 | 0 | 1 | 0 |
| 3/3' (upstream) | 1 | 1 | 1 | 0 | 0 | 0 | 0 |
| 4/4' (middle) | 0 | 0 | 0 | 1 | 1 | 1 | 0 |
| 5/5' (downstream) | 0 | 0 | 0 | 0 | 0 | 0 | 1 |
| Location of the problem | A | B | C | D | E | F | G |

Figure 3:
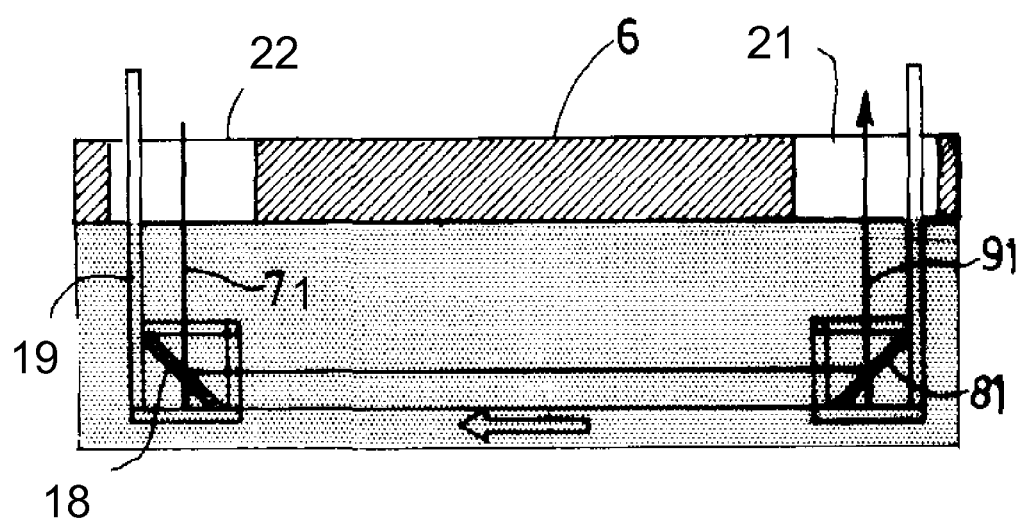

FIG. 3 illustrates the use of mirrors for guiding the beam along the longitudinal wall of the tank 6. The beam 71 is introduced into the tank 6 via a sighting window 22; it is then perpendicular to the direction of the flow of the glass (arrow) in the tank 6. A mirror 18 held by an arm 19 introduced via the sighting window 22 is placed on the path of the beam 71 and oriented at 45° to the latter so as to guide it perpendicularly to its initial course and parallel to the wall of the tank 6. Another mirror 81, held by an arm 91 introduced via another sighting window 21, is placed on the path of the beam so as to guide it perpendicularly to the wall of the tank 6 and to cause it to exit via the window 21. This use is of particular use in the downstream part of the tank placed downstream of the central shoulder of the tank.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A method for measuring a quantity in a furnace, comprising the steps of:
providing a device comprising:
an arm (7), a first end of which supports a box:
the wall of said box placed facing the second end of the arm is transparent,
within which is placed a backreflecting means capable of receiving a light beam originating from the first end of the arm and parallel to said arm and of returning it in the opposite direction parallel to the incident optical path,
a transparent screen attached to the second end of the arm so as to face the transparent wall of the box, and
a means for cooling the arm and the box;
directing a light beam from an emitter through the transparent screen parallel to the arm and through the transparent wall along the incident optical path;
allowing the light beam directed through the transparent wall to be reflected by the backreflector and returned through the transparent wall in the opposite direction parallel to the incident optical path;
receiving the returned light beam with a receiver;
introducing gas close to the surfaces of the transparent wall and of the transparent screen and optionally in the box; and
measuring a quantity in the furnace with at least one analyzer based on absorption spectroscopy using the returned light beam received by the receiver.

2. The method in claim 1, characterized in that the box and the transparent screen are attached perpendicularly to the arm.

3. The method as claimed in claim 1, characterized in that the analyzer is a laser diode.

4. The method as claimed in claim 1, characterized in that the quantity is chosen from: the concentration of a chemical compound or the temperature of the atmosphere in the furnace.

5. The method as claimed in claim 1, characterized in that the furnace is a glass melting furnace.

* * * * *